United States Patent [19]

Hershenson

[11] 4,267,318

[45] May 12, 1981

[54] 1-(DIARYLMETHYL)-4-PIPERIDINAMINE AND DERIVATIVES THEREOF

[75] Inventor: Fred M. Hershenson, Morton Grove, Ill.

[73] Assignee: G. D. Searle & Co., Chicago, Ill.

[21] Appl. No.: 74,641

[22] Filed: Sep. 12, 1979

[51] Int. Cl.$^3$ ..................... C09B 55/00; C07D 211/56
[52] U.S. Cl. ................................... 542/422; 542/424; 546/223; 546/197; 546/194
[58] Field of Search ............... 546/223, 197, 194, 192; 542/422, 424

[56] References Cited

U.S. PATENT DOCUMENTS

| | | | |
|---|---|---|---|
| 3,101,341 | 8/1963 | Cusic et al. | 546/223 |
| 3,158,609 | 11/1964 | Hamilton et al. | 546/223 |
| 3,531,487 | 9/1970 | Berger et al. | 546/223 |

FOREIGN PATENT DOCUMENTS

| | | | |
|---|---|---|---|
| 6703315 | 9/1967 | Netherlands | 546/223 |
| 6701679 | 9/1968 | South Africa | 546/223 |
| 1404868 | 9/1975 | United Kingdom | 546/223 |

OTHER PUBLICATIONS

Acta Pol Pharm, 34 (3), pp. 241-244 (1977).
C. R. Craig, Arch. Int. Pharmacodynither, 165 (2), pp. 328-336, (1977).
Index Chemicus, vol. 68, Issue 738, Abstract 265900 (1978).

Primary Examiner—Henry R. Jiles
Assistant Examiner—Robert C. Whittenbaugh
Attorney, Agent, or Firm—Dragan J. Karadzic; W. Dennis Drehkoff

[57] ABSTRACT

1-(Diarylmethyl)-4-piperidinamine and derivatives thereof of the formula

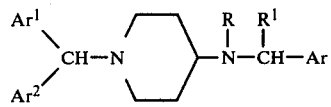

or a non-toxic pharmocologically acceptable acid addition salt thereof; wherein Ar, Ar$^1$ and Ar$^2$ independently are phenyl, phenyl substituted with up to five halogens, alkyl radicals of 1 to 7 carbon atoms or alkoxy radicals of 1 to 7 carbon atoms, 3,4-(methylenedioxy)-phenyl or pyridyl optionally substituted with up to four alkyl radicals of 1 to 7 carbon atoms; and R and R$^1$ are each hydrogen or together form a double bond between the nitrogen and carbon atoms to which they are attached are disclosed. These compounds are useful because of their anti-convulsant and anti-ulcer activity.

20 Claims, No Drawings

1-(DIARYLMETHYL)-4-PIPERIDINAMINE AND DERIVATIVES THEREOF

The present invention relates to 1-(diarylmethyl)-4-piperidinamine and derivatives thereof having the following general formula

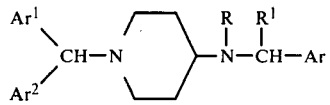

or a non-toxic pharmacologically acceptable acid addition salt thereof; wherein Ar, $Ar^1$ and $Ar^2$ independently are phenyl, phenyl substituted with up to five halogens, alkyl radicals of 1 to 7 carbon atoms or alkoxy radicals of 1 to 7 carbon atoms, 3,4-(methylenedioxy)-phenyl or pyridyl optionally substituted with up to four alkyl radicals of 1 to 7 carbon atoms; and R and $R^1$ are each hydrogen or together form a double bond between the nitrogen and carbon atoms to which they are attached.

The alkyl radicals of 1 to 7 carbon atoms contemplated in the above formula are methyl, ethyl, propyl, butyl, pentyl, hexyl, heptyl and the branched-chain isomers thereof, with methyl being preferred.

The alkoxy radicals of 1 to 7 carbon atoms contemplated in the above formula are methoxy, ethoxy, propoxy, butoxy, pentyloxy, hexyloxy, heptyloxy and the branched-chain isomers thereof, with methoxy being preferred The halogens contemplated in the above formula are bromine, chlorine, fluorine and iodine, with chlorine being preferred. The position of the substituents on the phenyl radicals contemplated in the above formula relative to the point of attachment of the phenyl radicals, or where more than one are present, to each other is not critical, and more than one type of substituent (for example, alkyl and halogen) can be present.

The point of attachment of the pyridyl nucleus to the adjacent methyl or methylene in the above formula and the disposition of any alkyl radical substituting the nucleus, both with respect to said point of attachment and to each other (when a plurality are present) is not critical. Thus, 2-pyridyl, 3-pyridyl, and 4-pyridyl, each optionally alkylated ad libitum, are all within the scope of this invention.

A particularly preferred embodiment of this invention is a compound of the formula

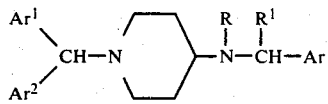

or a non-toxic pharmacologically acceptable acid addition salt thereof; wherein Ar, R and $R^1$ are as previously defined, and $Ar^1$ and $Ar^2$ independently are phenyl, phenyl substituted with up to five halogens, alkyl radicals of 1 to 7 carbon atoms or alkoxy radicals of 1 to 7 carbon atoms, or 3,4-(methylenedioxy)phenyl and of this embodiment a compound in which Ar is pyridyl optionally substituted with up to four alkyl radicals of 1 to 7 carbon atoms is further preferred.

The embodiment of the present invention of the formula

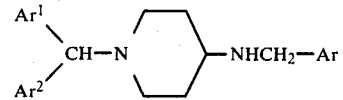

or a non-toxic pharmacologically acceptable acid addition salt thereof, wherein Ar, $Ar^1$ and $Ar^2$ are as previously defined is the preferred embodiment.

Another preferred embodiment is a compound to the formula

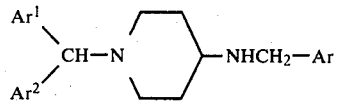

or a non-toxic pharmacologically acceptable acid addition salt thereof, wherein Ar, $Ar^1$ and $Ar^2$ independently are phenyl or phenyl substituted with up to five halogens, alkyl radicals of 1 to 7 carbon atoms or alkoxy radicals of 1 to 7 carbon atoms, with a compound of the formula

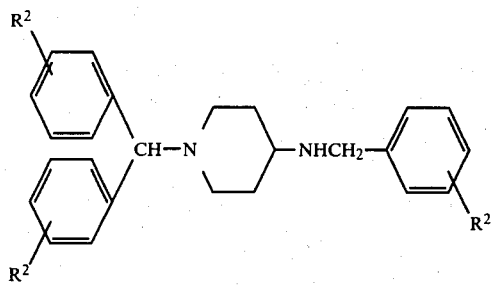

or a non-toxic pharmacologically acceptable acid addition salt thereof; wherein each $R^2$ independently is hydrogen, halogen, alkyl radical of 1 to 7 carbon atoms or alkoxy radical of 1 to 7 carbon atoms being further preferred.

Another preferred embodiment of this invention is a compound of the formula

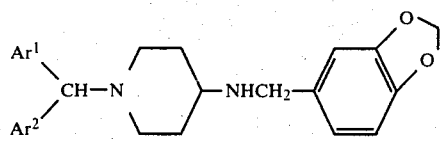

or a non-toxic pharmacologically acceptable acid addition salt thereof; wherein $Ar^1$ and $Ar^2$ independently are phenyl or phenyl substituted with up to five halogens, alkyl radicals of 1 to 7 carbon atoms or alkoxy radicals of 1 to 7 carbon atoms, with a compound of the formula

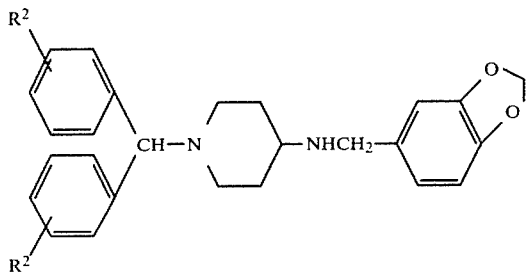

or a non-toxic pharmacologically acceptable acid addition salt thereof, wherein each R² independently is hydrogen, halogen, alkyl radical of 1 to 7 carbon atoms or alkoxy radical of 1 to 7 carbon atoms being further preferred.

Another preferred embodiment of this invention is a compound of the formula

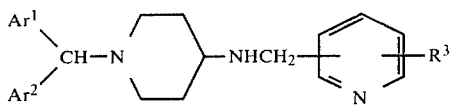

or a non-toxic pharmacologically acceptable acid addition salt thereof, wherein Ar¹ and Ar² independently are phenyl or phenyl substituted with up to five halogens, alkyl radicals of 1 to 7 carbon atoms or alkoxy radicals of 1 to 7 carbon atoms and R³ is hydrogen or alkyl radical of 1 to 7 carbon atoms, with a compound of the formula

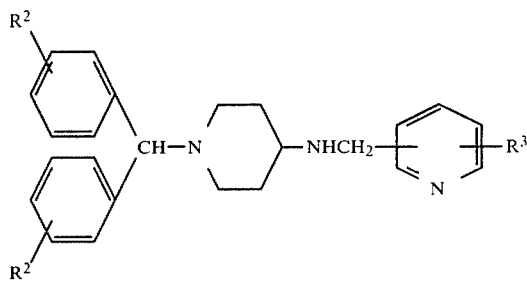

or a non-toxic pharmacologically acceptable acid addition salt thereof, wherein each R² independently is hydrogen, halogen, alkyl radical of 1 to 7 carbon atoms or alkoxy radical of 1 to 7 carbon atoms, and R³ is hydrogen or alkyl radical of 1 to 7 carbon atoms being further preferred.

Another preferred embodiment of this invention is a compound of the formula

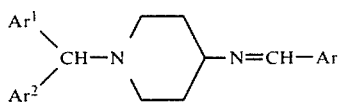

wherein Ar, Ar¹ and Ar² independently are phenyl, phenyl substituted with up to five halogens, alkyl radicals of 1 to 7 carbon atoms or alkoxy radicals of 1 to 7 carbon atoms, 3,4-(methylenedioxy)phenyl or pyridyl optionally substituted with up to four alkyl radicals of 1 to 7 carbon atoms.

Another preferred embodiment of this invention is a compound of the formula

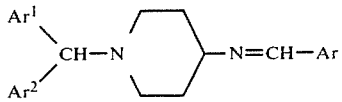

wherein Ar, Ar¹ and Ar² independently are phenyl or phenyl substituted with up to five halogens, alkyl radicals of 1 to 7 carbon atoms or alkoxy radicals of 1 to 7 carbon atoms, with a compound of the formula

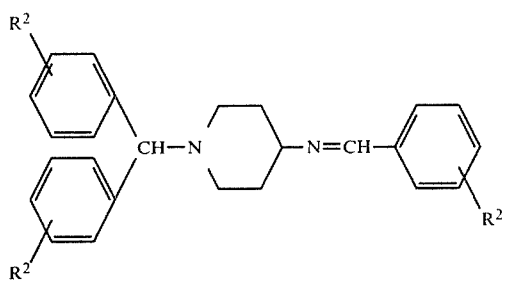

wherein each R² independently is hydrogen, halogen, alkyl radical of 1 to 7 carbon atoms or alkoxy radical of 1 to 7 carbon atoms being further preferred.

Another preferred embodiment of this invention is a compound of the formula

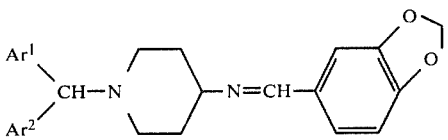

wherein Ar¹ and Ar² independently are phenyl or phenyl substituted with up to five halogens, alkyl radicals of 1 to 7 carbon atoms or alkoxy radicals of 1 to 7 carbon atoms, with a compound of the formula

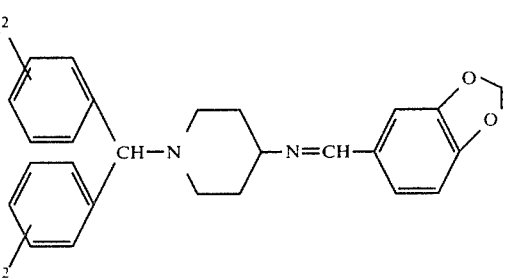

wherein each R² independently is hydrogen, halogen, alkyl radical of 1 to 7 carbon atoms or alkoxy radical of 1 to 7 carbon atoms being further preferred.

Another preferred embodiment of this invention is a compound of the formula

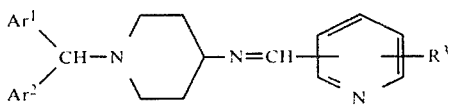

wherein Ar¹ and Ar² independently are phenyl or phenyl substituted with up to five halogens, alkyl radicals of 1 to 7 carbon atoms or alkoxy radicals of 1 to 7 carbon atoms; and R³ is hydrogen or alkyl radical of 1 to 7 carbon atoms, with a compound of the formula

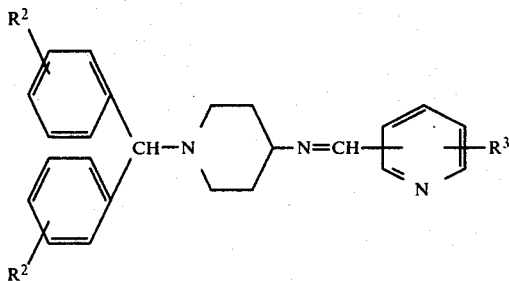

wherein each $R^2$ independently is hydrogen, halogen, alkyl radical of 1 to 7 carbon atoms or alkoxy radical of 1 to 7 carbon atoms; and $R^3$ is hydrogen or alkyl radical of 1 to 7 carbon atoms being further preferred.

The organic bases of this invention form non-toxic acid addition salts with a variety of organic and inorganic acids. Such salts are formed with acids such as sulfuric phosphoric, hydrochloric, hydrobromic, hydriodic, sulfamic, citric, lactic, maleic, malic, succinic, tartaric, cinnamic, acetic, benzoic, gluconic, ascorbic and related acids.

The compounds of the present invention are useful because of their pharmacological properties. In particular they are useful as anti-convulsant and anti-ulcer agents.

The anti-ulcerogenic utility of the instant compounds can be demonstrated via a standardized test for the capacity of a substance to inhibit the ulceration in rats, substantially as described in U.S. Pat. No. 3,798,268. Representative compounds of this invention—1-(diphenylmethyl)-N-[(6-methyl-2-pyridyl)methyl]-N-piperidinamine maleate, 1-(diphenylmethyl)-N-[3,4-(methylenedioxy)benzyl]-4-piperidinamine maleate, 1-(diphenylmethyl)-N-(phenylmethylene)-4-piperidinamine, and 1-(diphenylmethyl)-N-[3,4-(methylenedioxy)-benzylidene]-4-piperidinamine—are found active in this test at the dose of 50 mg/kg The anti-convulsant activity of the instant compounds can be demonstrated via a standardized test for the capacity of a substance to prevent the convulsion induced in mice by electoral shock, substantially as described in U.S. Pat. No. 3,937,701 except that a current of 50 mA was used to induce electroshock seizures. Representative compounds of the present invention—1-(diphenylmethyl)-N-[(6-methyl-2-pyridyl)methyl]-4-piperidinamine maleate, 1-(diphenylmethyl)-N-[(4-pyridyl)methyl]-4-piperidinamine, 1-(diphenylmethyl)-N-[3,4-(methylenedioxy)benzyl]-4-piperidinamine maleate, and 1-(diphenylmethyl)-N-[(4-pyridyl)methylene]-4-piperidinamine—are found active at the dose of 50 mg/kg, 50 mg/kg, 50 mg/kg and 100 mg/kg, respectively.

For therapeutic purposes, the substances of this invention can ordinarily be combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al.; "Remington's Pharmaceutical Sciences", 14 Ed., Merck Publishing Company, Eaton, Pa., 1965. Appropriate dosages, in any given instances, of course, depend upon the nature and severity of the condition treated, the route of administration, and the species of mammal involved, including its size and any individual idiosyncrasies which obtain.

Compounds of the present invention are conveniently prepared by the methods set out in Scheme I. Wherein Ar, Ar¹ and Ar² are as previously defined, and Hal is halogen.

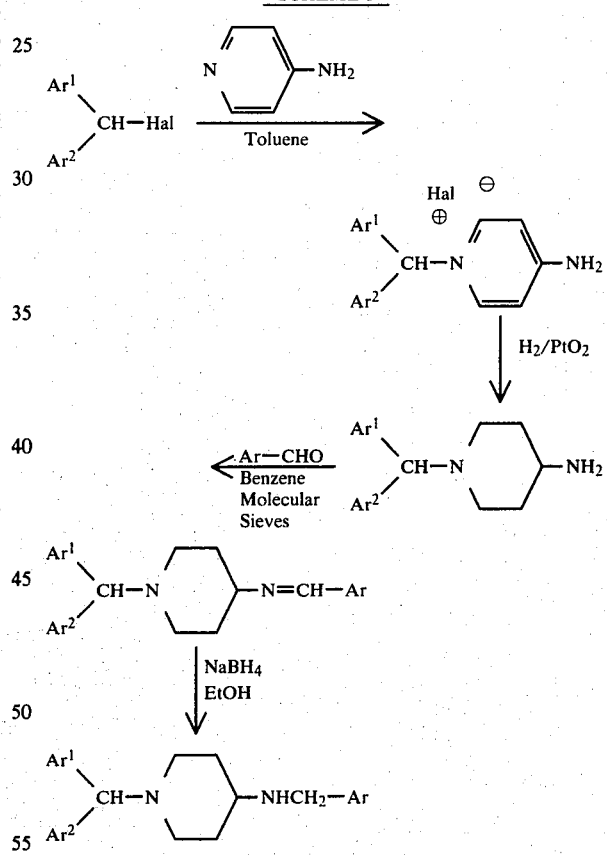

Conversion of the bases of this invention to corresponding acid addition salts is accomplished by admixture with one equivalent of any suitable organic or inorganic acid. The salts, in turn are converted to corresponding bases by contacting with excess alkali.

The examples which follow describe in detail compounds illustrative of the present invention and methods which have been devised for their preparation. It will be apparent to those skilled in the art that many modifications, both of materials and methods, may be practiced without departing from the purpose and intention of this disclosure. In these examples, temperatures are given in degrees centigrade (°C.) and quantities of materials in parts by weight unless parts by volume is specified. The relationship between parts by weight and parts by volume is the same as that existing between grams and milliliters.

EXAMPLE 1

A mixture of 38 parts of 4-aminopyridine, 100 parts of bromodiphenylmethane and 500 parts by volume of acetonitrile is heated at reflux temperature for about three hours with stirring. The reaction mixture is filtered, the solid obtained washed with 125 parts by volume of hot acetonitrile and air-dried overnight at room temperature. The obtained solid is recrystallized from 500 parts by volume of ethanol to yield 4-amino-1-(diphenylmethyl)pyridinium bromide, as a colorless crystalline solid melting at about 260°–262° C. This compound has the following formula.

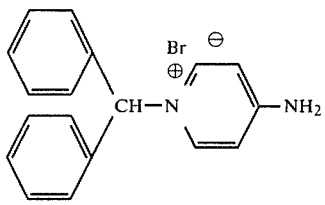

To a solution of 15.5 parts of 4-amino-1-(diphenylmethyl)-pyridinium bromide in 600 parts by volume of methanol is added 1.6 part of platinum dioxide catalyst and the resulting mixture is shaken with hydrogen at 60 psi pressure and room temperature for forty-two hours. The catalyst is then removed by filtration and the filtrate evaporated to dryness in vacuo. The residue is suspended in 200 parts by volume of 10% sodium carbonate solution and extracted with three 200 parts by volume portions of methylene chloride. The methylene chloride extracts are combined, dried over anhydrous sodium sulfate and evaporated to dryness in vacuo. The solid residue obtained is triturated with 250 parts by volume of anhydrous ethyl ether, filtered and the filtrate evaporated to yield 1-(diphenylmethyl)-4-piperidinamine, as a colorless solid melting at about 84°–95° C. This compound is represented by the following structural formula.

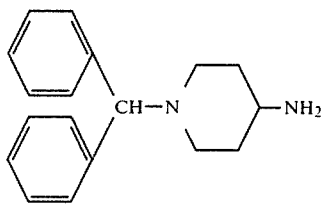

Substitution of an equivalent quantity of the appropriate bromodiarylmethane for bromodiphenylmethane called for in the procedure of the preceding paragraph 1, and substantially repeating the procedure of the preceding two paragraphs, the following compounds are obtained:

1-[(2-methylphenyl)phenylmethyl]-4-piperidinamine;
1-[(2-methylphenyl) (4-methylphenyl)methyl]-4-piperidinamine;
1-[(3-methoxyphenyl)phenylmethyl]-4-piperidinamine;
1-[(2-ethylphenyl) (4-methoxyphenyl)methyl]-4-piperidinamine;
1-[(2-ethoxyphenyl) (4-methoxyphenyl)methyl]-4-piperidinamine;
1-[(2-chlorophenyl)phenylmethyl]-4-piperdinamine;
1-[(3,4-dichlorophenyl)phenylmethyl]-4-piperidinamine;
1-[(4-bromophenyl) (2-chlorophenyl)methyl]-4-piperidinamine;
1-[(2-chlorophenyl) (4-methylphenyl)methyl]-4-piperidinamine;
1-[(2-chlorophenyl) (4-methoxyphenyl)methyl]-4-piperidinamine;
1-[(3-methylphenyl)phenylmethyl]-4-piperidinamine;
1-[(4-ethylphenyl) (3-methylphenyl]-4-piperidinamine;
1-[(4-ethylphenyl) (3,4-dimethylphenyl)methyl]-4-piperidinamine;
1-[(2-chlorophenyl) (3-chlorophenyl)methyl]-4-piperidinamine;
1-[(4-ethoxyphenyl) (3-methoxyphenyl)methyl]-4-piperidinamine;
1-[(3-methoxyphenyl) (4-methylphenyl)methyl]-4-piperidinamine;
1-[(2-chlorophenyl) (4-methylphenyl)methyl]-4-piperidinamine;
1-[(2-chlorophenyl) (3-methoxyphenyl)methyl]-4-piperidinamine;
1-[(4-chlorophenyl) (2-methylphenyl)methyl]-4-piperidinamine;
1-[(4-chlorophenyl) (4-methoxyphenyl)methyl]-4-piperidinamine;
1-[(4-ethylphenyl)phenylmethyl]-4-piperidinamine; and
1-[(2-ethoxyphenyl) (2-methoxyphenyl)methyl]-4-piperidinamine.

EXAMPLE 2

To a solution of 2.65 parts of 1-(diphenylmethyl)-4-piperidinamine in 20 parts by volume of benzene is added at room temperature a solution of 1.25 part of 6-methyl-2-pyridinecarboxaldehyde in 20 parts by volume of benzene. The resultant reaction mixture is stirred at room temperature for about 30 minutes, then refluxed for about 90 minutes, cooled to room temperature and allowed to stand overnight at room temperature. The solvent is then removed by evaporation and the residue triturated with 100 parts by volume of n-hexane to yield after filtration, 1-(diphenylmethyl)-N-[(6-methyl-2-pyridyl)methylene]-4-piperidinamine as a colorless solid melting at about 150°–152° C. This compound is represented by the following structural formula

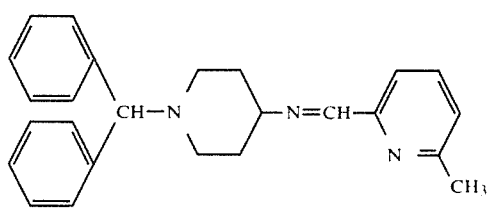

EXAMPLE 3

To a solution of 2.65 parts of 1-(diphenylmethyl)-4-piperidinamine in 20 parts by volume of benzene is added at a room temperature a solution of 1.10 part of 4-pyridinecarboxaldehyde in 20 parts by volume of benzene. The resultant reaction mixture is stirred at room temperature for about 30 minutes, then 2 parts of magnesium.sulfate added to the mixture and the stirring continued at room temperature for additional 60 minutes. The resultant mixture is filtered, the solvent removed and the residue triturated with 100 parts by volume of n-hexane to yield after filtration 1-(diphenylmethyl)-N-[(4-pyridyl)methylene]-4-piperidinamine as slightly yellow crystalline solid melting at about 183°–190° C. This compound is represented by the following structural formula

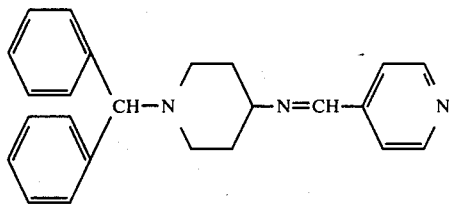

EXAMPLE 4

Substitution of an equivalent quantity of 1-[(2-methylphenyl)-phenylmethyl]-4-piperidinamine for 1-(diphenylmethylphenyl)-4-piperidinamine called for in Example 2 and substantial repetition of the procedure detailed therein, affords 1-[(2-methylphenyl)phenylmethyl]-N-[(4-pyridyl)methylene]-4-piperidinamine having the following structural formula

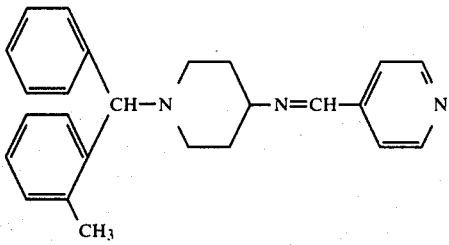

EXAMPLE 5

When an equivalent quantity of 1-[(2-methylphenyl)(4-methylphenyl)methyl]-4-piperidinamine is substituted in the procedure of Example 1, there is obtained 1-[(2-methylphenyl)(4-methylphenyl)methyl]-N-[(6-methyl-2-pyridyl)methylene]-4-piperidinamine having the following structural formula.

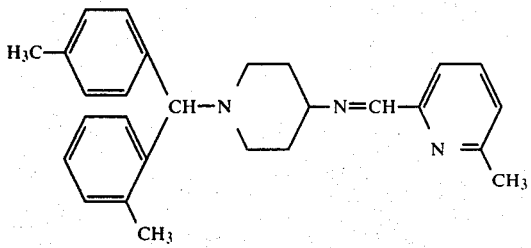

EXAMPLE 6

When equivalent quantities of 1-[(3-methoxyphenyl)-phenylmethyl]-4-piperidinamine and 6-ethyl-2-pyridinecarboxaldehyde are substituted in the procedure of Example 1, there is obtained 1-[(3-methoxyphenyl)phenylmethyl]-N-[(6-ethyl-2-pyridyl)methylene]-4-piperidinamine having the following structural formula

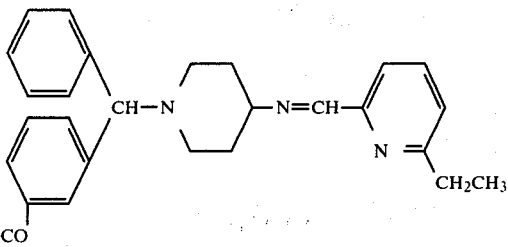

EXAMPLE 7

When an equivalent quantity of 1-[(2-ethylphenyl)(4-methoxyphenyl)methyl]-4-piperidinamine is substituted in the procedure of Example 2, there is obtained 1-[(2-ethylphenyl)(4-methoxyphenyl)methyl]-N-[(4-pyridyl)-methylene]-4-piperidinamine having the following structure formula

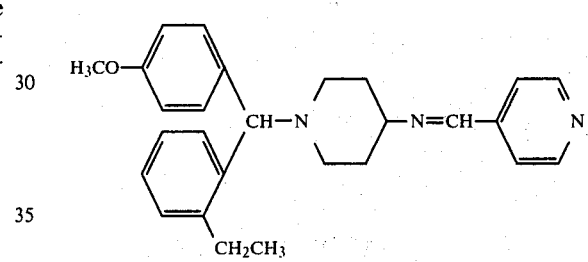

EXAMPLE 8

When an equivalent quantity of 1-[(2-ethoxyphenyl)(4-methoxyphenyl)methyl]-4-piperidinamine is substituted in the process of Example 2, there is obtained 1-[(2-ethoxyphenyl)(4-methoxyphenyl)methyl]-N-[(4-pyridyl)methylene]-4-piperidinamine having the following structural formula

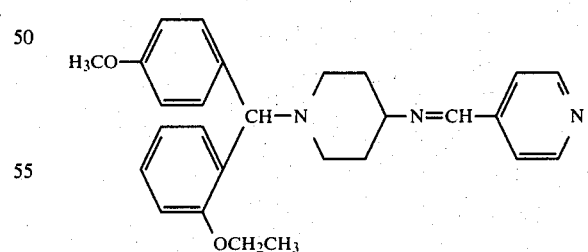

EXAMPLE 9

When equivalent quantities of 1-[(2-chlorophenyl)-phenylmethyl]-4-piperidinamine and 2-pyridinecarboxaldehyde are substituted in the procedure of Example 1, there is obtained 1-[(2-chlorophenyl)phenylmethyl]-N-[(2-pyridyl)methylene]-4-piperidinamine having the following structural formula

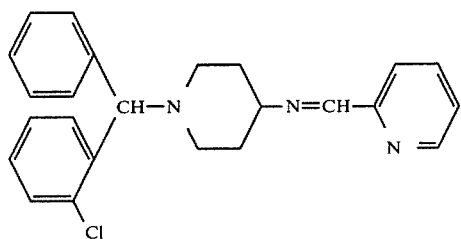

EXAMPLE 10

When an equivalent quantity of 1-[(3,4-dichlorophenyl)phenylmethyl]-4-piperidinamine is substituted in the procedure of Example 2, there is obtained 1-[(3,4-dichlorophenyl)phenylmethyl]-N-[(4-pyridyl)methylene]-4-piperidinamine having the following structural formula

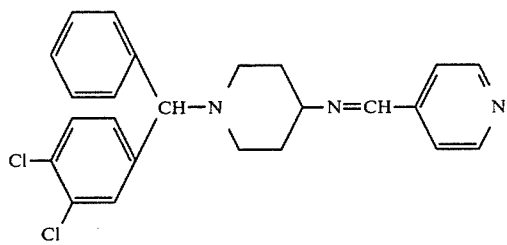

EXAMPLE 11

When an equivalent quantities of 1-[(4-bromophenyl)(2-chlorophenyl)methyl]-4-piperidinamine and 2-pyridinecarboxaldehyde are substituted in the procedure of Example 1, there is obtained 1-[(4-bromophenyl)(2-chlorophenyl)methyl]-N-[(2-pyridyl)methylene]-4-piperidinamine having the following structural formula

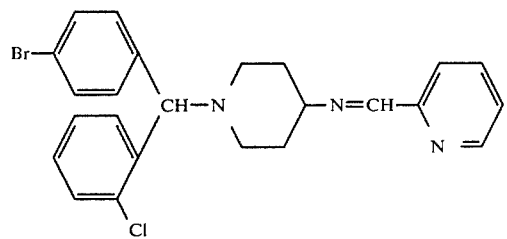

EXAMPLE 12

When equivalent quantities of 1-[(3-chlorophenyl)(4-methylphenyl)methyl]-4-piperidinamine and 2-pyridinecarboxaldehyde are substituted in the procedure of Example 1, there is obtained 1-[(3-chlorophenyl)(4-methylphenyl)methyl]-N-[(2-pyridyl)methylene]-4-piperidinamine having the following structural formula.

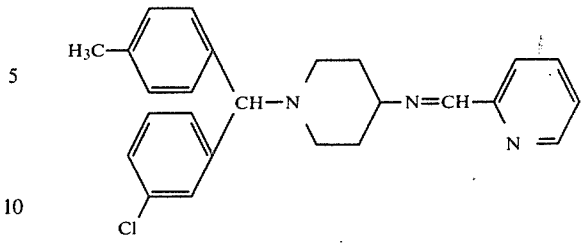

EXAMPLE 13

When equivalent quantities of 1-[(2-chlorophenyl)(4-methoxyphenyl)methyl]-4-piperidinamine and 2-pyridinecarboxaldehyde are substituted in the procedure of Example 1, there is obtained 1-[(2-chlorophenyl)(4-methoxyphenyl)methyl]-N-[(2-pyridyl)methylene]-4-piperidinamine having the following structural formula.

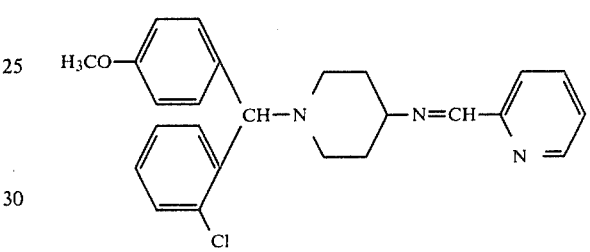

EXAMPLE 14

A solution of 4 parts of 1-(diphenylmethyl)-4-piperidinamine, 1.6 part of benzaldehyde and 75 parts by volume of benzene is heated at reflux temperature on a steam bath for about 60 minutes and then anhydrous magnesium sulfate is added to the mixture. The mixture is heated a few more moments and then filtered. The filtrate is evaporated to dryness in vacuo and the solid residue triturated with n-hexane to yield, after filtration, 1-(diphenylmethyl)-N-(phenylmethylene)-4-piperidinamine as a colorless solid melting at about 141°–143° C. This compound has the following structural formula

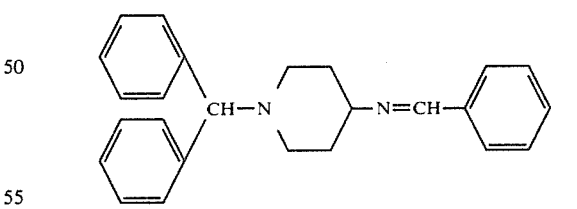

When equivalent quantities of the appropriate 1-(diarylmethyl)-4-piperidinamine and benzaldehyde are substituted in the above detailed procedure, the following compounds are obtained:

1-[(3-methylphenyl)phenylmethyl]-N-(phenylmethylene)-4-piperidinamine;
1-[(4-ethylphenyl)(3-methylphenyl)methyl]-N-(phenylmethylene)-4-piperidinamine;
1-[(4-ethylphenyl)(3,4-dimethylphenyl)methyl]-N-[(2-methylphenyl)methylene]-4-piperidinamine;
1-[(2-chlorophenyl)phenylmethyl]-N-(phenylmethylene)-4-piperidinamine;

1-[(2-chlorophenyl)(3-chlorophenyl)methyl]-N-(phenylmethylene)-4-piperidinamine;
1-[(3,4-dichlorophenyl)phenylmethyl]-N-(phenylmethylene)-4-piperidinamine;
1-[(3-methoxyphenyl)phenylmethyl]-N-(phenylmethylene)-4-piperidinamine;
1-[(4-ethoxyphenyl)(3-methoxyphenyl)methyl]-N-(phenylmethylene)-4-piperidinamine;
1-[(3-methoxyphenyl)(4-methylphenyl)methyl]-N-(phenylmethylene)-4-piperidinamine;
1-[(2-chlorophenyl)(4-methylphenyl)methyl]-N-(phenylmethylene)-4-piperidinamine;
1-[(2-chlorophenyl)(3-methoxyphenyl)methyl]-N-(phenylmethylene)-4-piperidinamine;
1-(diphenylmethyl)-N-[(4-chlorophenyl)methylene]-4-piperidinamine;
1-[(4-chlorophenyl)(2-methylphenyl)methyl]-N-[(4-chlorophenyl)methylene]-4-piperidinamine;
1-[(4-chlorophenyl)(2-methylphenyl)methyl]-N-[(3-methoxyphenyl)methylene]-4-piperidinamine; and
1-[(4-chlorophenyl)(4-methoxyphenyl)methyl]-N-[(4-methylphenyl)methylene]-4-piperidinamine;

EXAMPLE 15

A solution of 4 parts of 1-(diphenylmethyl)-4-piperidinamine, 2.25 parts of 3,4-(methylenedioxy)benzaldehyde and 75 parts by volume of benzene is heated at reflux temperature with stirring for about two hours. Anhydrous magnesium sulfate is then added to the reaction mixture, the mixture filtered and the filtrate evaporated to dryness in vacuo. The solid residue is triturated with n-hexane to yield, after filtration, 1-(diphenylmethyl)-N-[3,4-(methylenedioxy)benzylidene]-4-piperidinamine, as a colorless solid melting at about 158°–160° C. This compound has the following structural formula.

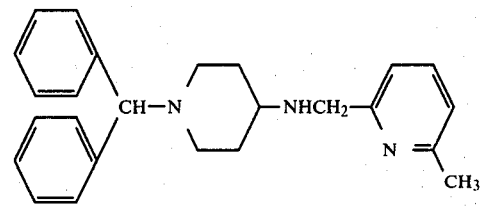

When an equivalent quantity of the appropriate 1-(diarylmethyl)-4-piperidinamine is substituted in the above detailed procedure, there are obtained the following compounds:

1-[(2-chlorophenyl)phenylmethyl]-N-[3,4-(methylenedioxy)benzylidene]-4-piperidinamine;
1-[(2-chlorophenyl)(3-chlorophenyl)methyl]-N-[3,4-(methylenedioxy)benzylidene]-4-piperidinamine;
1-[(3,4-dichlorophenyl)phenylmethyl]-N-[3,4-(methylenedioxy)benzylidene]-4-piperidinamine;
1-[(3-methylphenyl)phenylmethyl]-N-[3,4-(methylenedioxy)benzylidene]-4-piperidinamine;
1-[(4-ethylphenyl)(3-methylphenyl)methyl]-N-[3,4-(methylenedioxy)benzylidene]-4-piperidinamine;
1-[(4-ethylphenyl)phenylmethyl]-N-[3,4-(methylenedioxy)benzylidene]-4-piperidinamine;
1-[(4-ethylphenyl)(3,4-dimethylphenyl)methyl]-N-[3,4-(methylenedioxy)benzylidene]-4-piperidinamine;
1-[(3-methoxyphenyl)phenylmethyl]-N-[3,4-(methylenedioxy)benzylidene]-4-piperidinamine;
1-[(4-ethoxyphenyl)(3-methoxyphenyl)]-N-[3,4-(methylenedioxy)benzylidene]-4-piperidinamine;
1-[(3-methoxyphenyl)(4-methylphenyl)methyl]-N-[3,4-(methylenedioxy)benzylidene]-4-piperidinamine;
1-[(2-chlorophenyl)(4-methylphenyl)methyl]-N-[3,4-(methylenedioxy)benzylidene]-4-piperidinamine; and
1-[(2-chlorophenyl)(3-methoxyphenyl)methyl)methyl]-N-[3,4-(methylenedioxy)benzylidene]-4-piperidinamine.

EXAMPLE 16

A mixture of 5.55 parts of 1-(diphenylmethyl)-N-[(6-methyl-2-pyridyl)methylene]-4-piperidinamine, 1.9 part of sodium borohydride and 250 parts by volume of ethanol is stirred at room temperature for about two hours. The reaction mixture is evaporated to dryness in vacuo, the residue partitioned between 200 parts by volume of water and 150 parts by volume of methylene chloride and the layers separated. The aqueous layer is extracted with additional 125 parts by volume of methylene chloride. The methylene chloride fractions are combined, washed with 200 parts by volume of water, dried over anhydrous sodium sulfate, filtered and evaporated to dryness in vacuo to yield, as a yellow oil, 1-(diphenylmethyl)-N-[(6-methyl-2-pyridyl)methyl]-4-piperidinamine. This compound has the following formula

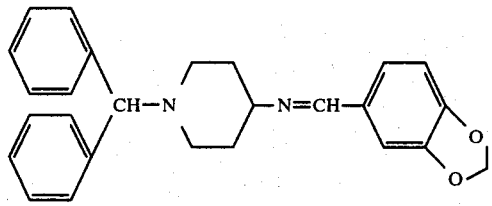

When an equivalent quantity of the appropriate 1-(diarylmethyl)-N-[(2-pyridyl)methylene]-4-piperidinamine is substituted in the above-detailed procedure, there is obtained:

1-[(2-methylphenyl)(4-methylphenyl)methyl]-N-[(6-methyl-2-pyridyl)methyl]-4-piperidinamine;
1-[(3-methoxyphenyl)phenylmethyl]-N-[(6-ethyl-2-pyridyl)methyl]-4-piperidinamine;
1-[(2-chlorophenyl)phenylmethyl]-N-[(2-pyridyl)methyl]-4-piperidinamine;
1-[(4-bromophenyl)(2-chlorophenyl)methyl]-N-[(2-pyridyl)methyl]-4-piperidinamine;
1-[(3-chlorophenyl)(4-methylphenyl)methyl]-N-[(2-pyridyl)methyl]-4-piperidinamine; and
1-[(2-chlorophenyl)(4-methoxyphenyl)methyl]-N-[(2-pyridyl)methyl]-4-piperidinamine.

EXAMPLE 17

6 Parts of 1-(diphenylmethyl)-N-[(6-methyl-2-pyridyl)methyl]-4-piperidinamine is dissolved in 150 parts by volume of ethyl ether and to this solution is added 100 parts by volume of the saturated solution of maleic acid in ethyl ether. The resultant mixture is filtered, the solid washed three times with 100 parts by volume portions of ethyl ether and dried in vacuo overnight at 85° C. to yield 1-(diphenylmethyl)-N-[(6-methyl-2-pyridyl)methyl]-4-piperidinamine maleate, as colorless needless melting at about 190°–191° C. after recystallization from acetonitrile. This compound has the following structural formula.

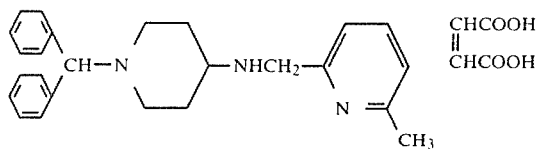

EXAMPLE 18

A suspension of 3.55 parts of 1-(diphenylmethyl)-N-[(4-pyridyl)methylene]-4-piperidinamine in 150 parts by volume of ethanol, stirred at room temperature, is treated with 1 part of sodium borohydride. The resultant reaction mixture is stirred at room temperature for about three hours, then evaporated to dryness in vacuo. The residue is partitioned between 100 parts by volume of water and 100 parts by volume of chloroform and the layers separated. The aqueous layer is extracted with additional 100 parts by volume of chloroform and the chloroform layers combined. The combined chloroform fraction is washed with 150 parts by volume of water, dried over anhydrous sodium sulfate and evaporated to dryness to yield 1-(diphenylmethyl)-N-[(4-pyridyl)methyl]-4-piperidinamine which melts, after recrystallization from n-hexane, at about 138°–162° C. This compound is represented by the following structural formula.

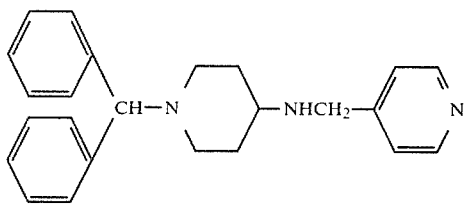

When an equivalent quantity of the appropriate 1-(diarylphenyl)-N-[(4-pyridyl)methylene]-4-piperidinamine is substituted in the above-detailed procedure, there is obtained:
1-[(2-methylphenyl)phenylmethyl]-N-[(4-pyridyl)methyl]-4-piperidinamine;
1-[(2-ethylphenyl)(4-methoxyphenyl)methyl]-N-[(4-pyridyl)methyl]-piperidinamine;
1-[(2-ethoxyphenyl)(4-methoxyphenyl)methyl]-N-[(4-pyridyl)methyl]-4-piperidinamine; and
1-[(3,4-dichlorophenyl)phenylmethyl]-N-[(4-pyridyl)methyl]-4-piperidinamine.

EXAMPLE 19

A suspension of 4 parts of 1-(diphenylmethyl)-N-[3,4-(methylenedioxy)benzylidene]-4-piperidinamine in 100 parts by volume of ethanol, stirred at room temperature, is treated with 1 part of sodium borohydride. The resultant reaction mixture is stirred at room temperature overnight and evaporated to dryness in vacuo. The residue is partioned between 100 parts by volume of water and 100 parts by volume of chloroform and the layers separated. The acequeous layer is extracted with additional 100 parts by volume of chloroform and the chloroform layers combined. The combined chloroform fraction is washed with 150 parts by volume of water, dried over anhydrous sodium sulfate, filtered and evaporated to dryness in vacuo to yield, as a colorless oil, 1-(diphenylmethyl)-N-[3,4-(methylenedioxy)benzyl]-4-piperidinamine. This compound has the following formula

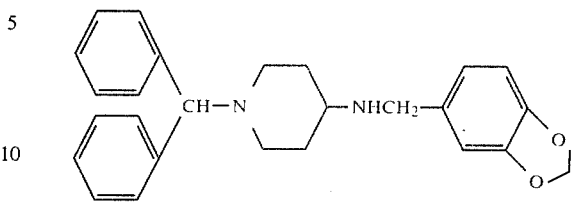

When an equivalent quantity of the appropriate 1-(diarylmethyl)-N-[3,4-(methylenedioxy)benzylidene]-4-piperidinamine is substituted in the above-detailed procedure, there is obtained:
1-[(2-chlorophenyl)phenylmethyl]-N-[3,4-(methylenedioxy)benzyl]-4-piperidinamine;
1-[(2-chlorophenyl)(3-chlorophenyl)methyl]-N-[3,4-(methylenedioxy)benzyl-4-piperidinamine;
1-[(3,4-dichlorophenyl)phenylmethyl]-N-[3,4-(methylenedioxy)benzyl]-4-piperidinamine;
1-[(3-methylphenyl)phenylmethyl]-N-[3,4-(methylenedioxy)benzyl]-4-piperidinamine;
1-[(4-ethylphenyl)(3-methylphenyl)methyl]-N-[3,4-(methylenedioxy)benzyl]-4-piperidinamine;
1-[(4-ethylphenyl)phenylmethyl]-N-[3,4-(methylenedioxy)benzyl]-4-piperidinamine;
1-[(4-ethylphenyl)(3,4-dimethylphenyl)methyl]-N-[3,4-(methylenedioxy)benzyl]-4-piperidinamine;
1-[(3-methoxyphenyl)phenylmethyl]-N-[3,4-(methylenedioxy)benzyl]-4-piperidinamine;
1-[(4-ethoxyphenyl)(3-methoxyphenyl)methyl]-N-[3,4-(methylenedioxy)benzyl]-4-piperidinamine;
1-[(3-methoxyphenyl)(4-methylphenyl)methyl]-N-[3,4-(methylenedioxy)benzyl]-4-piperidinamine;
1-[(2-chlorophenyl)(4-methylphenyl)methyl]-N-[3,4-(methylenedioxy)benzyl]-4-piperidinamine; and
1-[(2-chlorophenyl)(3-methoxyphenyl)methyl]-N-[3,4-(methylenedioxy)benzyl]-4-piperidinamine.

EXAMPLE 20

4.85 Parts of 1-(diphenylmethyl)-N-[3,4-(methylenedioxy)benzyl]-4-piperidinamine is dissolved in 150 parts by volume of anhydrous ethyl ether and to this solution is added a solution of 1.5 part of maleic acid in 150 parts by volume of ethyl ether. The resultant mixture is filtered, and the solid washed several times with ethyl ether. The solid is recrystallized from acetonitrile to yield, as colorless needles, 1-(diphenylmethyl)-N-[3,4-(methylenedioxy)benzyl]-4-piperidinamine maleate melting at about 190°–198° C. This compound has the following structural formula.

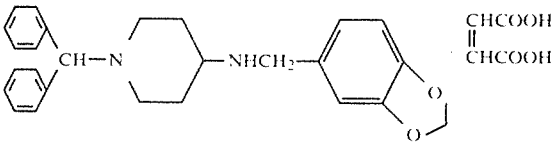

EXAMPLE 21

When an equivalent quantity of 1-(diphenylmethyl)-N-(phenylmethylene)-4-piperidinamine is substituted in the procedure of Example 18, there is obtained 1-(diphenylmethyl)-N-benzyl-4-piperidinamine which is represented by the following structural formula

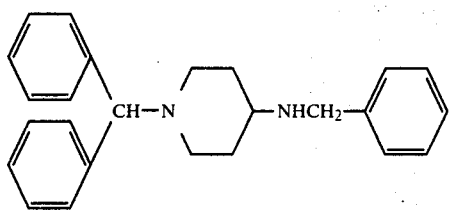

Substitution of an equivalent quantity of the appropriate 1-(diarylmethyl)-N-(arylmethylene)-4-piperidinamine in the procedure of Example 18 affords:

1-[(3-methylphenyl)phenylmethyl]-N-benzyl-4-piperidinamine;
1-[(4-ethylphenyl)(3-methylphenyl)-N-benzyl-4-piperidinamine;
1-[(4-ethylphenyl)(3,4-dimethylphenyl)methyl]-N-(2-methylbenzyl)-4-piperidinamine;
1-[(2-chlorophenyl)phenylmethyl]-N-benzyl-4-piperidinamine;
1-[(2-chlorophenyl)(3-chlorophenyl)methyl]-N-benzyl-4-piperidinamine;
1-[(3,4-dichlorophenyl)phenylmethyl]-N-benzyl-4-piperidinamine;
1-[(3-methoxyphenyl)phenylmethyl]-N-benzyl-4-piperidinamine;
1-[(4-ethoxyphenyl)(3-methoxyphenyl)methyl]-N-benzyl-4-piperidinamine;
1-[(3-methoxyphenyl)(4-methylphenyl)methyl]-N-benzyl-4-piperidinamine;
1-[(2-chlorophenyl)(4-methylphenyl)methyl]-N-benzyl-4-piperidinamine;
1-[(2-chlorophenyl)(3-methoxyphenyl)methyl]-N-benzyl-4-piperidinamine;
1-(diphenylmethyl)-N-(4-chlorobenzyl)-4-piperidinamine;
1-[(4-chlorophenyl)(2-methylphenyl)methyl]-N-(4-chlorobenzyl)-4-piperidinamine;
1-[(4-chlorophenyl)(2-methylphenyl)methyl]-N-(3-methoxybenzyl)-4-piperidinamine; and
1-[(4-chlorophenyl)(4-methoxyphenyl)methyl]-N-(4-methylbenzyl)-4-piperidinamine.

What is claimed is:
1. A compound of the formula

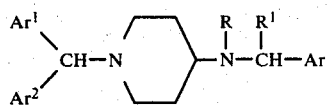

or a non-toxic pharmacologically acceptable acid addition salt thereof; wherein $Ar^1$ and $Ar^2$ independently are phenyl, phenyl substituted with up to five halogens, alkyl radicals of 1 to 7 carbon atoms or alkoxy radicals of 1 to 7 carbon atoms, 3,4-(methylenedioxy)phenyl or pyridyl optionally substituted with up to four alkyl radicals of 1 to 7 carbon atoms; wherein Ar is an alkoxy radical of 1 to 7 carbon atoms, or pyridyl optionally substituted with up to four alkyl radicals of 1 to 7 carbon atoms; and R and $R^1$ are each hydrogen or together form a double bond between the nitrogen and carbon atoms to which they are attached.

2. A compound according to claim 1 having the formula

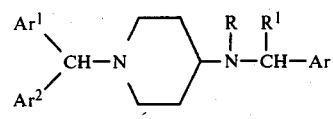

or a non toxic pharmacologically acceptable acid addition salt thereof; wherein Ar is pyridyl optionally substituted with up to four alkyl radicals of 1 to 7 carbon atoms; $Ar^1$ and $Ar^2$ independently are phenyl, phenyl substituted with up to five halogens, alkyl radicals of 1 to 7 carbon atoms or alkoxy radicals of 1 to 7 carbon atoms, or 3,4-(methylenedioxy)phenyl; and R and $R^1$ are each hydrogen or together form a double bond between the nitrogen and carbon atom to which they are attached.

3. A compound according to claim 1 having the formula

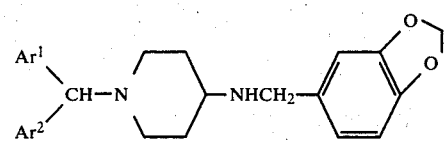

or a non-toxic pharmacologically acceptable acid addition salt thereof; wherein $Ar^1$ and $Ar^2$ independently are phenyl or phenyl substituted with up to five halogens, alkyl radicals of 1 to 7 carbon atoms or alkoxy radicals of 1 to 7 carbon atoms.

4. A compound according to claim 1 having the formula

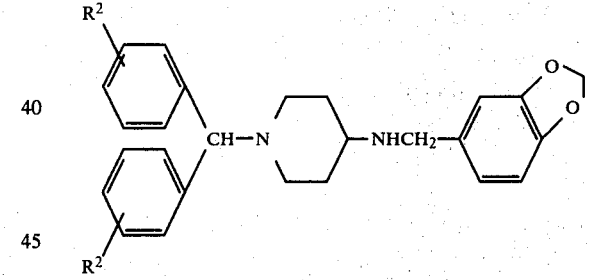

or a non-toxic pharmacologically acceptable acid addition salt thereof; wherein each $R^2$ independently is hydrogen, halogen, alkyl radical of 1 to 7 carbon atoms or alkoxy radical of 1 to 7 carbon atoms.

5. A compound according to claim 1 having the formula

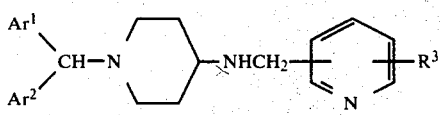

or a non-toxic pharmacologically acceptable acid addition salt thereof; wherein $Ar^1$ and $Ar^2$ independently are phenyl or phenyl substituted with up to five halogens, alkyl radicals of 1 to 7 carbon atoms or alkoxy radicals of 1 to 7 carbon atoms, and $R^3$ is hydrogen or alkyl radical of 1 to 7 carbon atoms.

6. A compound according to claim 1 having the formula

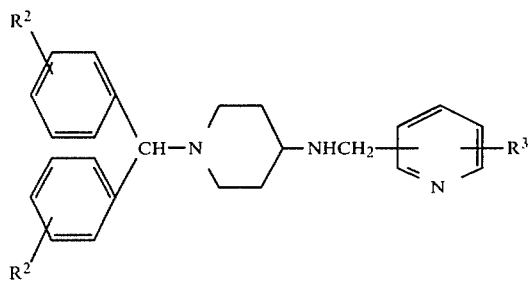

or a non-toxic pharmacologically acceptable acid addition salt thereof; wherein each $R^2$ independently is hydrogen, halogen, alkyl radical of 1 to 7 carbon atoms or alkoxy radical of 1 to 7 carbon atoms; and $R^3$ is hydrogen or alkyl radical of 1 to 7 carbon atoms.

7. A compound according to claim 1 which is 1-(diphenylmethyl)-N-[3,4-(methylenedioxy)benzyl]-4-piperidinamine or the maleic acid salt thereof.

8. A compound accordingly to claim 1 which is 1-(diphenylmethyl)-N-[(4-pyridyl)methyl]-4-piperidinamine.

9. A compound according to claim 1 which is 1-(diphenylmethyl)-N-[(6-methyl-2-pyridyl)methyl]-4-piperidinamine or the maleic acid salt thereof.

10. A compound according to claim 1 having the formula

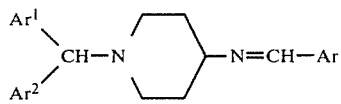

wherein Ar, $Ar^1$ and $Ar^2$ independently are phenyl, phenyl substituted with up to five halogens, alkyl radicals of 1 to 7 carbon atoms or alkoxy radicals of 1 to 7 carbon atoms, 3,4-(methylenedioxy)phenyl or pyridyl optionally substituted with up to four alkyl radicals of 1 to 7 carbon atoms.

11. A compound according to claim 10 having the formula

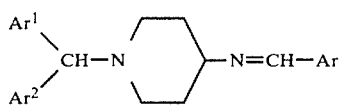

wherein Ar, $Ar^1$ and $Ar^2$ independently are phenyl or phenyl substituted with up to five halogens, alkyl radicals of 1 to 7 carbon atoms or alkoxy radicals of 1 to 7 carbon atoms.

12. A compound according to claim 10 having the formula

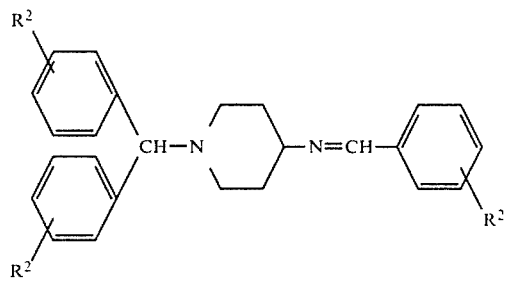

wherein each $R^2$ independently is hydrogen, halogen, alkyl radical of 1 to 7 carbon atoms or alkoxy radical of 1 to 7 carbon atoms.

13. A compound according to claim 1 having the formula

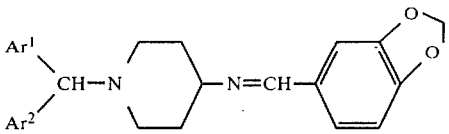

wherein $Ar^1$ and $Ar^2$ independently are phenyl or phenyl substituted with up to five halogens, alkyl radicals of 1 to 7 carbon atoms or alkoxy radicals of 1 to 7 carbon atoms.

14. A compound according to claim 10 having the formula

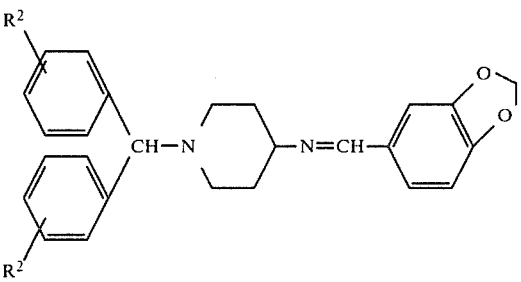

wherein each $R^2$ independently is hydrogen, halogen, alkyl radical of 1 to 7 carbon atoms or alkoxy radical of 1 to 7 carbon atoms.

15. A compound according to claim 10 having the formula

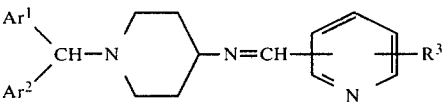

wherein $Ar^1$ and $Ar^2$ independently are phenyl or phenyl substituted with up to five halogens, alkyl radicals of 1 to 7 carbon atoms or alkoxy radicals of 1 to 7 carbon atoms; and $R^3$ is hydrogen or alkyl radical of 1 to 7 carbon atoms.

16. A compound according to claim 10 having the formula

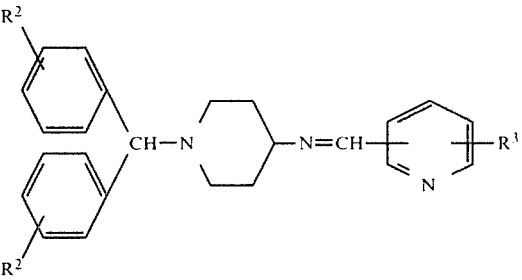

wherein each $R^2$ independently is hydrogen, halogen, alkyl radical of 1 to 7 carbon atoms or alkoxy radical of 1 to 7 carbon atoms; and $R^3$ is hydrogen or alkyl radical of 1 to 7 carbon atoms.

17. A compound according to claim 10 which is 1-(diphenylmethyl)-N-[(6-methyl-2-pyridyl)methylene]-4-piperidinamine.

18. A compound according to claim 10 which is 1-(diphenylmethyl)-N-[(4-pyridyl)methylene]-4-piperidinamine.

19. A compound according to claim 10 which is 1-(diphenylmethyl)-N-(phenylmethylene)-4-piperidinamine.

20. A compound according to claim 10 which is 1-(diphenylmethyl)-N-[3,4-(methylenedioxy)benzylidene]-4-piperidinamine.

* * * * *